US007610192B1

(12) United States Patent
Jamieson

(10) Patent No.: US 7,610,192 B1
(45) Date of Patent: Oct. 27, 2009

(54) PROCESS AND SYSTEM FOR HIGH PRECISION CODING OF FREE TEXT DOCUMENTS AGAINST A STANDARD LEXICON

(76) Inventor: Patrick William Jamieson, 10172 Parkshore Dr., Fishers, IN (US) 46038

( * ) Notice: Subject to any disclaimer, the term of this patent is extended or adjusted under 35 U.S.C. 154(b) by 497 days.

(21) Appl. No.: 11/386,996

(22) Filed: Mar. 22, 2006

(51) Int. Cl.
G06F 17/27 (2006.01)
G06F 17/20 (2006.01)
G06F 7/00 (2006.01)
G06Q 50/00 (2006.01)

(52) U.S. Cl. .............................. 704/9; 704/1; 707/104.1; 705/2

(58) Field of Classification Search ........................ None
See application file for complete search history.

(56) References Cited

U.S. PATENT DOCUMENTS

| | | | |
|---|---|---|---|
| 6,182,029 B1* | 1/2001 | Friedman ........................ 704/9 |
| 6,438,533 B1* | 8/2002 | Spackman et al. ............. 706/45 |
| 6,529,876 B1 | 3/2003 | Dart et al. | |
| 6,915,254 B1* | 7/2005 | Heinze et al. ................... 704/9 |
| 2002/0128816 A1* | 9/2002 | Haug et al. ..................... 704/4 |
| 2002/0198739 A1 | 12/2002 | Lau et al. | |
| 2003/0018470 A1 | 1/2003 | Golden et al. | |
| 2004/0220895 A1 | 11/2004 | Carus et al. | |
| 2004/0243545 A1 | 12/2004 | Boone et al. | |
| 2005/0240439 A1* | 10/2005 | Covit et al. ..................... 705/2 |
| 2006/0020493 A1 | 1/2006 | Cousineau et al. | |
| 2007/0088559 A1* | 4/2007 | Kim .............................. 705/1 |

OTHER PUBLICATIONS

Zieman, Y. Bleich, H. "Conceptual Mapping of User's Queries to Medical Subject Headings" Proc AMIA Fall Symp. 1997: 519-22.*

(Continued)

*Primary Examiner*—Matthew J Sked

(57) ABSTRACT

Coding free text documents, especially in medicine, has become an urgent priority as electronic medical records (EMR) mature, and the need to exchange data between EMRs becomes more acute. However, only a few automated coding systems exist, and they can only code a small portion of the free text against a limited number of codes. The precision of these systems is low and code quality is not measured. The present invention discloses a process and system which implements semantic coding against standard lexicon(s) with high precision. The standard lexicon can come from a number of different sources, but is usually developed by a standard's body. The system is semi-automated to enable medical coders or others to process free text documents at a rapid rate and with high precision. The system performs the steps of segmenting a document, flagging the need for corrections, validating the document against a data type definition, and looking up both the semantics and standard codes which correspond to the document's sentences. The coder has the option to intervene at any step in the process to fix mistakes made by the system. A knowledge base, consisting of propositions, represents the semantic knowledge in the domain. When sentences with unknown semantics are discovered they can be easily added to the knowledge base. The propositions in the knowledge base are associated with codes in the standard lexicon. The quality of each match is rated by a professional who understands the knowledge domain. The system uses this information to perform high precision coding and measure the quality of the match.

25 Claims, 11 Drawing Sheets

OTHER PUBLICATIONS

Wright, L. Nardini, H. Aronson, A. Rindflesch, Thomas. Hierarchical Concept Indexing of Full-Text Documents in the Unified Medical Language System Information Sources Map, Journal of American Society for Information Science, 1999; 514-23.*

Volk, M. Ripplinger, B. Vintar, S. Buitelaar, P. Raileanu, D. Sacaleanu, B. Semantic Annotation for Concept-based cross-language medical information retrieval, Int'l Journal of Medical Information 67 2002; 97-112.*

Campbell KE, Oliver D, Spackman, KA, Shortliffe, EH. Representing Thoughts, Words, and Things in the UMLS. Jamia. 1998; 5:421-431.].

Kin Wah Fung, KW, Hole, WT, Nelson, SJ, Srinivasan, S et. al. Integrating SNOMED CT into the UMLS: An Exploration of Different Views of Synonymy and Quality of Editing. J Am Med Inform Assoc. 2005; 12:486-494.

Penz JF, Brown SH, Carter JS, Elkin PL, Nguyen VN, Sims SA, Lincoln MJ. Evaluation of SNOMED coverage of Veterans Health Administration terms. Medinfo. 2004; 11(Pt 1): 540-4.

Rebholz-Schuhmann D, Kirsch H, Couto F (2005) Facts from text—Is text mining ready to deliver? PLoS Biol 3(2): e65.

Mack R. et al. Text analytics for life science using the Unstructured Information Management Architecture. IBM Systems Journal. Sep. 2004.

* cited by examiner

SNOMED Coder

Segmentation

Report | Code Page | Snomed Page

Snomed Concepts

| Include | Proposition | Match Quality | Snomed ConceptId | Proposition Phrase |
|---|---|---|---|---|
| ☑ | The breasts are almost entirely fatty. | Good | 129716005 | breasts almost entirely fatty |
| ☑ | There are no suspicious lesions. | Good | 163614007 | suspicious |
| | | | 373067005 | no |
| ☑ | There are no suspicious lesions. | Good | 4975003 | lesion |
| ☑ | There is no evidence of breast malignancy. | Good | 41647002 | no evidence |
| ☑ | There is no evidence of breast malignancy. | Good | 254837009 | malignant tumor of breast |

Snomed Qualified Name: Almost entirely fat breast composition (finding)  ← 311

Snomed Concepts

| Include | Proposition | Match Quality | Snomed ConceptId | Proposition Phrase |
|---|---|---|---|---|
| ▷ | The heart size is normal. | Good | 246115007 | size |
| ▷ | The bony thorax is normal. | Good | 298720006 | finding of bone of thorax |
| ▷ | The bony thorax is normal. | Good | 17621005 | normal |
| ▷ | There are no pulmonary infiltrates. | Good | 128309002 | radiologic infiltrates |
| ▷ | There are no pulmonary infiltrates. | Good | 373067005 | no |
| ▷ | There are no pleural effusions. | Good | 373067005 | no |
| ▷ | There are no pleural effusions. | Good | 60046008 | pleural effusion |
| ▷ | There airway is not grossly narrow. | Good | 373067005 | no |
| ▷ | There airway is not grossly narrow. | Good | 134223000 | narrow |
| ▶ | There airway is not grossly narrow. | Good | 44567001 | trachea |
| ▷ | There airway is not grossly narrow. | Good | 255344003 | gross |
| ▷ | Negative chest. | Good | 168733007 | negative chest x-ray |

Snomed Qualified Name: Tracheal structure (body structure)

Fig. 7

PROCESS AND SYSTEM FOR HIGH PRECISION CODING OF FREE TEXT DOCUMENTS AGAINST A STANDARD LEXICON

FEDERALLY SPONSORED RESEARCH

The invention described herein was funded in part by a grant from the National Library of Medicine, Grant # 1 R43LM008974-01. The United States Government may have certain rights to the invention.

CROSS REFERENCE TO RELATED APPLICATIONS

The following co-pending U.S. patent application is hereby fully incorporated by reference, "Process for constructing a semantic knowledge base using a document corpus", Ser. No. 10/844,912, filed on May 13, 2004.

SEQUENCE LISTING OR PROGRAM

None.

FIELD

The present invention relates to a method and system for coding free text documents using natural language processing, and more specifically semantic analysis.

BACKGROUND

Medical documents contain a wealth of biomedical information, but unfortunately 85% of this information is in free text and not accessible for data mining or analysis without expensive effort to read and code these documents. Although natural language programs have achieved a limited ability to extract and code medical findings, the capability to semantically process all the free text in a medical document has never been achieved in a large scale medical domain.

Health professionals increasingly believe the adoption of electronic medical records (EMR) will improve medical care by fostering the sharing of patient information. The federal government has taken a leadership role in this area, through the endorsement of standards for EMR interoperability. One component of EMR interoperability is a lexicon, which is a dictionary of standard terms, each assigned a unique identifier. The federal government has endorsed the following standard lexicons for EMR data exchange: (1) The College of American Pathologists Systematized Nomenclature of Medicine Clinical Terms (SNOMED CT) for laboratory result contents, non-laboratory interventions and procedures, anatomy, diagnosis and problems, and nursing. (2) Health Level 7 (HL7) for demographic information, units of measure, immunizations, and clinical encounters. (3) Laboratory Logical Observation Identifier Name Codes (LOINC) for laboratory test orders and drug label section headers, and (4) the Health Insurance Portability and Accountability Act (HIPAA) transactions and code sets for electronic exchange of health related information in billing and administrative functions. Other standard code sets have been devised or are being created, which will further facilitate the transfer of electronic health information.

While the adoption of standards is desirable and necessary for medical information exchange, new challenges arise that were much smaller problems in the world of "paper" based records. Under the old paradigm there was a limited expectation of receiving codified information. The government and insurance companies received codified data to pay claims against two standard code sets: (1) Current Procedural Terminology (CPT) published by the American Medical Association, which describes services rendered by physicians, and consists of 8,568 codes and descriptors and (2) International Classification of Diseases, Ninth Revision, Clinical (ICD-9-CM) published by the Center for Medicare and Medicaid Services (Federal Agency), which describes diagnoses and procedures, and consists of; approximately 17,000 codes.

Currently, health information coders, using narrative information from diagnoses and procedures provided by physicians and other recognized practitioners, assign codes to medical reports using these two standard code sets. Coding is necessary for reimbursement of patient services, and coding errors can lead to denial of payment. Because the government puts a great deal of emphasis on thorough and correct coding, and given that even these relatively small code sets are complicated to use, a large consulting and software industry supports health information coders.

The government's push to promote robust but more complex coding standards will require new technology to assist coders. Health and Human Secretary Thompson announced in that SNOMED CT would be free to use by all U.S. health providers under a license agreement between the federal government and the College of American Pathologists. The National Library of Medicine paid for this nationwide license because they believed the SNOMED CT lexicon will serve as key clinical language standard for the national health information infrastructure; however, there are few medical coders that can code an entire medical document against SNOMED CT.

The SNOMED CT system is several orders of magnitude more complex to use than CPT or ICD-9-CM. As of early 2006, there were 368,000 unique terms in SNOMED CT. Unlike CPT or ICD-9-CM, SNOMED codes can also define relationships between concepts. For example, the concept of fracture of shaft of tibia can be qualified by laterality (laterality=right) and by fracture type (fracture type=spiral). SNOMED calls this post-coordination. There are three types of post-coordination: refinement, qualification, and combination. One problem with post-coordination is the opportunity to designate multiple valid sequences of codes to describe the same clinical concept. In the above example, if at a future time SNOMED creates two new "pre-coordinated" concepts, "fracture of shaft of the right tibia", and "fracture of shaft of the left tibia", a coder may use either the more specific code, "fracture of the shaft of the right tibia" or two codes "fracture of shaft of tibia" qualified by "right". This is a simple example, because the clinical concept is relatively straightforward. However, as the complexity of clinical concepts increases the number of valid SNOMED code sequences increase. This is undesirable for interoperability, data mining, and decision support. Yet, there are no good automated tools that fully address this problem.

Autocoders are software utilities that have been used to perform coding of medical records. Typical autocoders use a multi-step process consisting of word based tokenization, normalization, stemming, and token matching of medical expressions to concepts in a standard lexicon. Generally the best match is considered to be the one with the greatest number of shared tokens between the target phrase and the standard lexicon. Unfortunately, this approach is poorly suited to codifying the meaning of sentences that contain modifiers, qualifying clauses, or other implicit information. Simply put, the semantics of a sentence is more complex than the additive sum of its words.

Semantics is a complex field which looks at least two components of meaning, intensional and extensional. The physical objects to which the expression refers is the expression's extensional component, and the characteristic features of the physical object which are used to identify the object is the intensional component [CAMPBELL K E, OLIVER D, SPACKMAN, K A, SHORTLIFFE, E H. Representing Thoughts, Words, and Things in the UMLS. JAMIA. 1998; 5:421-431.] Understanding the expression's intensional and extensional components is essential to semantic representation. Only when the entire context is fully considered can synonymy be decided. For example, in the phrase, "Semi-Upright Portable film of the chest", an autocoder would match the token 'Semi-upright' to the SNOMED concept 'Semi-erect body position'. However, if the autocoder made this same match for the phrase, "A 45 degree semi-upright venographic table", it would be in error. The error is the result of failing to understand the intensional component of this phrase.

Accurate coding critically depends on synonymy. Names that have the same meaning should refer to the same concept. Unfortunately, rarely do two names have exactly the same meaning, because their semantics is often fuzzy. Names may closely overlap in meaning, but are not equivalent in all contexts. In some cases they may be practically synonymous, although they are not logically synonymous. For example, a physician may write, "There are diffuse pulmonary infiltrates." SNOMED would represent this as a post-coordinated sequence of two concepts: (1) 409609008—Radiologic infiltrate of the lung (disorder) and (2) 19648000—Diffuse (qualifier). However, a pulmonary infiltrate is a pathologic process independent of the means used to detect it. Nevertheless, because a chest x-ray is a common diagnostic tool for detecting pulmonary infiltrates, this sequence of SNOMED codes is close enough to the semantic meaning of this sentence. A medical expert is in the best position to judge whether this code sequence is "close enough". For high precision matching, human judgments are required to accurately determine the semantic equivalence between a sentence expression and concepts in a standard lexicon. Even experts may have trouble agreeing on the synonymy of clinical expressions [KIN WAH FUNG, K W, HOLE, W T, NELSON, S J, SRINIVASAN, S et. al. Integrating SNOMED CT into the UMLS: An Exploration of Different Views of Synonymy and Quality of Editing. J Am Med Inform Assoc. 2005; 12:486-494.] Therefore, even the best autocoders make mistakes, especially when they must return complex post-coordinated code sequences, because they lack domain knowledge. Current coding applications do not adequately address the problem of semantic equivalence.

An evaluation of two popular SNOMED autocoders was performed by the Veterans Administration Hospital and the Utah Department of Medical Informatics, Salt Lake City [Penz J F, Brown S H, Carter J S, Elkin P L, Nguyen V N, Sims S A, Lincoln M J. Evaluation of SNOMED coverage of Veterans Health Administration terms. Medinfo. 2004; 11 (Pt 1): 540-4]. They were interested only in the accuracy of the SNOMED autocoders to code for the pathologic diagnosis, and not every sentence in the report. Yet even for this limited task, the two autocoders completely agreed only 12% of the time, with partial agreement 82% of the time. Common reasons for partial matches were spelling errors and abbreviations in the target phrase. Expert review of the autocoders' accuracy showed that only in those cases in which the two SNOMED autocoders completely agreed was there high precision (88%) in coding. In the case of partial agreement, precision slipped to 50%. Additionally, neither SNOMED autocoder could assign a code to 6% of the diagnoses.

Consider the following sentence from a radiology report, "There is a right internal jugular line in place with the tip in the superior vena cava." The best sequence of SNOMED codes consists of: 405425001—Catheterization of internal jugular vein (procedure), 24028007—Right (qualifier value), 1872000—In (attribute), and 48345004 Superior Vena Cava Structure (body structure). Note that the semantics of "catheterization of the internal jugular vein" is not logically equivalent to "internal jugular line in place", but is closely related. Likewise the attribute, "in", refers to the "catheter tip", and not the entire catheter, yet, again there is a close relationship. Although an autocoder equipped with a very large synonym table might get some of these codes correct, the autocoder would lack the domain knowledge and judgment to determine the overall quality of this match. Autocoders do not have the ability to rate the quality of their semantic matches except through some arbitrary scoring algorithm. For example, an autocoder might assign a score of 0.8 if it could match 4 of the 5 significant words in the target phrase. This may have little relevance to the actual match quality as determined by a human reviewer, yet measuring code quality is vital to the coding industry.

Dart and Rawlins [U.S. Pat. No. 6,529,876] taught a method for generating Evaluation and Management (E&M) codes using electronic templates to gather the required information in a standardized fashion. However, their approach requires data be entered in a standardized form. Similar systems require data be input in predefined fields. These systems are unable to process non-standard input data, such as a free text. They place a significant data entry burden on the healthcare provider.

Cousineau et. al. [USPTO application 20060020493] discuss a method to "correct" non-standard, or free text input data, using a syntax processing block and a knowledge ontology to generate one or more healthcare billing codes. The details of using natural language processing to generate the "corrected" data file are not disclosed. The problem of semantic equivalence is not addressed.

Boone et. al. [USPTO application 20040243545, 20040220895] disclosed a system for automated coding. Their system uses a classification engine which depends on statistical models developed from training data. The statistical models vary with document type. Rules are added to perform additional filtering. Golden et. al. [USPTO application 20030018470] teaches a method for coding free text data using Hidden Markov Models and the Viterbi algorithm. However statistical approaches run into similar problems as autocoders, because there are no strong methods to guarantee or even measure semantic equivalence.

Lau et. al. [USPTO application 20020198739] teaches a system for mapping and matching laboratory results and tests. Their approach is dictionary based and does not perform semantic analysis at the sentence level.

A more sophisticated approach was disclosed by Heinze and Morsch [U.S. Pat. No. 6,915,254]. Their system employs a parser using syntactical and semantic rules that allow for more accurate coding than those with only employ computerized look-up tools. Phrases, clauses, and sentences are matched individually and in combination against knowledge-based vectors stored in a database. They describe a component called a resolver, which applies high-level medical coding rules to produce diagnosis, procedure, and EM level codes. Their resolver includes a knowledge base of severity and reimbursement values per code, code ordering rules, code mappings specific to particular payers, and which codes are not billed by particular providers or billed to particular payers. The heart of their natural language processing system is an engine that takes terms in free text, and matches them to vectors which consists of lists of valid word sequences for a specific concept. Although their system can process the free text associated with a subset of billing codes, it does not try to semantically process all the free text in the medical record. They do not propose a systematic method for deriving all the relevant concepts or extracting a comprehensive knowledge representation scheme for all the semantic knowledge contained in medical free text documents. Without this knowledge one can not completely code a medical document against a complex compositional lexicon such as SNOMED CT.

Another problem with prior art approaches is that some information is implicit in discourse, such as the connections between sentences and sentence constitutions. One type of implicitness is anaphora, which occurs when an abbreviated linguistic form can only be understood by reference to additional context; the reference is called 'anaphora', and the mention of the entity to which anaphora refers is called the 'antecedent'.

Consider the following radiology report. Source: RIGHT, TWO VIEWS. Description: There is a nondisplaced spiral fracture of the distal fibula. Ankle mortise radiographically stable. Impression: Reduction maintained since June. In this case the 'reduction' refers to the spiral fracture, so the last sentence could more clearly state, "Reduction of the spiral fracture of the distal fibula maintained since June." Unfortunately, busy physicians rarely have the time to completely specify all their antecedents. While a human reader would have no trouble resolving the ambiguity of this sentence, it is far more challenging for a computer. Although there are many active investigators in the field of anaphora resolution, and several promising techniques, there is no general algorithm to solve this problem. Yet, without addressing this problem, high precision coding is impossible.

A high precision coding system requires a deep understanding of the knowledge domain. It must squarely address how to identify linguistic expressions that are semantically equivalent, a difficult problem, since computational linguists have not yet developed tools which can analyze more than 30% of English sentences and transform them into structured forms [Rebholz-Schuhmann D, Kirsch H. Couto F (2005) Facts from text—Is text mining ready to deliver? PLOS Biol 3(2): e65]. Without identifying most or all of the linguistic variations that represent the same statement semantically, the coding system will have suboptimal precision.

A major hurdle to providing this deeper level of knowledge is discovering all the relevant concepts in a circumscribed area of knowledge—a domain. Few tools and methods are available to systematically categorize domain knowledge, especially in medium to large scale domains. IBM researchers built a tool, BioTeKS, capable of highlighting some semantic categories and their relations using automated annotators [Mack R. et al. Text analytics for life science using the Unstructured Information Management Architecture. IBM Systems Journal. September, 2004], but could not extract the detailed semantic relationships found in medical documents without having domain experts construct and refine finite state grammar rules, which have been shown to be difficult to construct, and rarely complete except in very simple domains.

For all these reasons, the high precision coding system of the present invention does not exist in the current art. Significant features of the system include: (1) a deep understanding of the knowledge contained in the documents being encoded, (2) mapping semantically equivalent linguistic expressions to a logical structure called a proposition, so that standard codes which represent this knowledge are consistent (both now and in the future), (3) resolving anaphora, (4) using human judgments to make the best possible match between semantic propositions and codes in the standard lexicon, (5) judging the quality of a coding matches, and (6) using software tools to make the process maximally efficient while at the same time very precise. Prior art systems do not meet these demanding requirements

OBJECTS AND ADVANTAGES

The present invention has been developed because there are no available solutions for high precision coding of all the free text in a medical document against large, standard, compositional lexicons such as SNOMED CT. One use of the present invention is to enable heterogeneous computer systems to be able to freely exchange free text data using logically correct semantics. The current art does not provide for efficient means to take free text documents, and with minimal effort map the free text to concepts in a standard lexicon. Such a system would be valuable in text mining, decision support, and billing. It is therefore a primary object of the present invention to provide a novel method and system for coding free text documents against third party standard lexicons.

A related object of this invention is an intuitive display which enables a user to easily segment free text, correct spelling errors, and validate document structure, prior to coding so the resulting codes are more precise.

Yet another object of this invention is an interface that allows an editor to mark up a free text document to resolve anaphora and other ambiguities while maintaining the original document text, so coding is more accurate.

Another object of this invention is a display of semantic "propositions" derived from sentences in the document and their corresponding text lines. These propositions describe an invariant way to represent the semantic knowledge of the document's sentences, so if at a future time the codes in the standard lexicon are changed, the document's codes can be simply updated.

Still another object of the present invention is a method to show which sentences are not understood by the system, or have unknown semantics. These sentences can be added to a table of unique sentences and mapped to propositions in the semantic knowledge base, and finally codes in the standard lexicon. The system is therefore easily extensible and able to incorporate new knowledge.

An object of this invention is a means to select or exclude sentence(s) for code mapping. This allows for skipping sentences which would potentially violate patient or doctor confidentially if transmitted to a third party, or violate the Health Insurance Portability and Accountability Act (HIPAA).

Yet another object of the invention is a user interface that displays codes from the standard lexicon which match the meaning of sentences in the free text document, and displays the quality of the match. A related object provides a means for these codes to be selected and stored in a database or exported to another information system.

Finally, an object of the present invention is a utility for building the correspondence (mapping) between logical propositions, which contain the semantic knowledge in a document, and codes in the standard lexicon with a minimum of effort.

SUMMARY OF THE INVENTION

The present invention provides a process for high precision coding of free text documents against large standard lexicons.

These lexicons could be government endorsed, created by standard committees, or obtained from a variety of sources, and may be either pre-coordinated or compositional. The process consist of (1) segmenting the document into headers and sentences, (2) correcting word spelling, expanding abbreviations, and validating document structure, (3) resolving ambiguous references, (4) mapping sentences to semantic propositions and (5) mapping semantic propositions to codes in the standard lexicon. In accordance with one illustrative embodiment, the coding system employs a visual interface design, which enables a user to easily isolate document headers, perform sentence segmentation, make spelling and other corrections, and resolve ambiguities prior to semantic mapping. The coding system matches each sentence to semantic proposition(s) and allows the user to decide whether these proposition(s) should be coded against the standard lexicon. The system further identifies sentences that have unknown semantics, and allows a knowledge engineer to add semantic knowledge to a knowledge base prior to coding. Another aspect of the present invention enables the user to see what codes in the standard lexicon match their semantic propositions and free text sentences, and the quality of the match. The user can then decide to include these codes in a database or export them as part of the document's metadata. Although the examples are taken from the medical domain, the process and system are general and can be used in any knowledge domain that can be reasonably circumscribed by a large document collection.

DRAWINGS

These and other features of the Subject Invention will be better understood in relation to the Detailed Description taken in conjunction with the drawings, of which:

FIG. 1 is a bitmap rendering of a computer screen displaying one embodiment of a computer interface showing the raw free text of a medical report segmented into headers and sentences.

FIG. 2 is a bitmap rendering of a computer screen displaying one embodiment of a computer interface demonstrating the result of mapping the sentences in FIG. 1 to semantic propositions.

FIG. 3 is a bitmap rendering of a computer screen displaying one embodiment of a computer interface depicting the result of a mapping the propositions in FIG. 2 to codes and code descriptions in the SNOMED CT lexicon.

FIG. 4 is a bitmap rendering of a computer screen displaying one embodiment of a computer interface showing a free text sentence from a medical report that does not have corresponding semantic proposition(s).

FIG. 5 is a bitmap rendering of a computer screen displaying one embodiment of a computer interface illustrating the sentence of FIG. 4 mapped by a knowledge engineer to a semantic proposition using a knowledge editor.

FIG. 6 is a bitmap rendering of a computer screen displaying one embodiment of a computer interface showing the operation of a utility which facilitates the mapping of propositions to codes in a standard lexicon, for this example SNOMED CT.

FIG. 7 is a bitmap rendering of a computer screen displaying one embodiment of a computer interface showing the output of SNOMED CT codes from the example in FIG. 5 and FIG. 6.

FIG. 8 is the bitmap rendering of a computer screen displaying one embodiment of a computer interface demonstrating a sentence that has been annotated by a medical coder with additional information to resolve ambiguous anaphora.

FIG. 9 is a block diagram of the components of the current invention.

FIG. 10 is a flowchart of the process for creating the mapping tables used by the proposition and code look up engines in FIG. 9.

FIG. 11 is a flowchart of the inventive coding process using the components shown in FIG. 9, illustrating the steps of coding a free text report using against codes in a standard lexicon.

Understanding that these drawings depict only typical embodiments of the invention and are not to be construed to limit its scope, the invention will be described in detail below.

DETAILED DESCRIPTION OF THE PREFERRED EMBODIMENTS

While the present invention is contemplated for use in a wide variety of application domains, it is described herein, primarily in the context of a medical information coding system in radiology for the purpose of illustration only.

The present invention employs several knowledge base components described in application Ser. No. 10/844,912 titled, "Process for constructing a semantic knowledge base using a document corpus, herein referred to as "corpus based knowledge construction". Briefly, that invention describes the steps for mapping the set S of sentences in a corpus of related documents, to the set M, of unique meanings or propositions in a knowledge domain to form a semantic knowledge base. A knowledge domain is the semantic knowledge contained in a large corpus of related documents from the domain, for example the semantic knowledge in 500,000 radiology reports. The fundamental unit asserted in the semantic knowledge base is a proposition expressed as a declarative sentence, conveying the underlying meaning of a document sentence. Propositions are distinct from the sentences that convey them, although they are related. For example, the sentences "The chest x-ray is normal" and "The chest x-ray is within normal limits" map to the same proposition or meaning. The knowledge-base designer creates propositions in a semi-automated fashion by drawing from common sentences in the corpus using software tools. By mapping sentence variants with the same meaning to the same proposition, the semantic equivalence of different free text sentences is accurate because strong methods of string matching are used, over weaker statistical methods. Propositions and sentence mappings are systematically created to fully characterize the semantic knowledge of a domain. The current invention uses the unique sentence table, the semantic knowledge base, and a proposition mapping table that associates free text sentences with their underlying propositions from this earlier work.

The following definitions may be useful.

| | Definition List 1 |
|---|---|
| Term | Definition |
| Proposition | Atomic unit of semantic meaning capturing in whole or part the knowledge within a declarative sentence. |
| Knowledge domain | The set of all propositions that represent the knowledge within a specialized field of study such as radiology as derived from a document corpus. Also known as the knowledge base, or semantic knowledge base. |
| Corpus | A large collection of related documents |

-continued

Definition List 1

| Term | Definition |
|---|---|
| | or reports from which a semantic knowledge base can be derived. Also known as a document collection. |
| Semantic Annotation | The process of taking a sentence from a document corpus or a new document and assigning one or more meanings represented by propositions in a semantic knowledge base. If no close proposition(s) is found creating the proposition(s) prior to assignment. Also known as semantic analysis. |
| Knowledge Engineer | A skilled professional who can create new propositions and semantically annotate sentences. |
| Proposition Mapping Table | A table, usually in the form of a relational database table, which contains the links between unique sentences from the corpus and their semantic proposition(s). |
| Semantic Hierarchy | A taxonomic arrangement of semantic propositions, using knowledge categories. |
| Subsumption | The arrangement of knowledge in which the most general ideas (propositions) of the knowledge domain are presented at a higher level and progressively differentiated propositions are displayed at a lower level. |
| Lexicon | A dictionary of terms, consisting of either a single word or a multi-word combination where each term is uniquely identified with a specific code. |
| Standard Lexicon | A lexicon developed by a third party, such as a standards body, for data encoding and exchange. |
| Pre-coordinated Lexicon | A type of lexicon in which all the words in a term form a single unit with a single code. |
| Compositional Lexicon | A type of lexicon in which several terms can be combined to represent the information in a complex concept using multiple codes. |
| Representative Medical Lexicons | SNOMED CT (Systematicized Nomenclature of Medicine, Clinical Terminology), ICD (International Classification of Diseases), 9th Edition, Clinical Modification, (ICD-9-CM), ICD-10, HCPCS (Health Care Financing Administration Common Procedure Coding System), NDC (National Drug Codes), CPT (Current Procedural Terminology), CDPN (Code on Dental Procedures and Nomenclature), UMLS (Unified Medical Language System), LOINC (Logical Observation Identifiers, Names, and Codes), DIN (Drug Identification Numbers), DRGs (Diagnosis Related Groups). |
| Code Mapping Table | A table, usually in the form of a relational database table, which holds the links between unique propositions from a corpus, and codes in the standard lexicon. |
| Code Annotation | The process of taking a proposition in a semantic knowledge base and assigning one or more codes from the standard lexicon. |
| Segmentation | The process of breaking a document into headers and sentences. The process may be manual, automatic, or both. |
| Segmented document | A document that has been delimited into headers and sentences. |
| Correction | The process for checking a document for inconsistencies such as misspellings, incorrect format, or missing information. Sometimes referred to as normalization. |

-continued

Definition List 1

| Term | Definition |
|---|---|
| Corrected document | A document where corrections have been made. |
| Anaphora | An abbreviated linguistic form that can only be understood by reference to its antecedent context. |
| Resolution | The process of creating more specific sentence expressions in order to disambiguate anaphora. |
| Resolved document | A document which has undergone resolution. |
| Document Type Definition | A set of rules, usually in the form of a grammar, for judging the conformance of a document. |
| Validation | The process of determining whether a document conforms to a document type definition and/or meets rule based criteria for acceptability. |
| Validated Document | A document that has satisfactorily passed through the validation process. |
| Coding | The process of matching propositions and codes from a standard lexicon to sentences in the document. |
| Coded Document | A document that has been coded. |
| Metadata | Information added to a document that defines various properties (such as its semantics), but remaining outside the actual written text. |

Overview

The invention assigns codes from a standard lexicon (including SNOMED CT, ICD-9, CPT, LOINC, and other lexicons) to computer readable physician reports through a semi-automated process. The invention allows government agencies, insurance companies, researchers, and medical billing companies to quickly and inexpensively assign medical codes to every sentence of interest in a medical report. The preferred implementation will assist human medical coders to determine and assign these codes, but if the end user will accept lower precision, the invention can assign codes in a fully automated manner. The preferred implementation envisages the coding to take place through a service bureau (such as a web service) so there are only minor modifications in medical work flow. However, it could be implemented using a desktop computer.

For the purpose of illustration, the free text document, which is analyzed by the present invention, is a radiology report (or, simply, "report") created shortly after a patient has had an imaging examination interpreted by a radiologist. Such notes today are commonly transcribed, or generated by speech recognition programs, but occasionally they are directly input into a computer. The present invention is capable of accepting reports from a variety of sources. The preferred embodiment analyzes the free text in plain ASCII format, but it would work equally well if created by a word processor. No matter how much the report is corrected or annotated, it is always first archived in its original format.

The first step in the process takes the raw text and segments it into headers and sentences. Both automated and manual methods are used as will be described in greater detail. The segmented text is displayed in a separate window so that a medical coder can view each sentence on a separate line, making it easier to perform corrections and add annotations. Corrections include fixing spelling and syntax, and expanding abbreviations. The system can be configured to perform most corrections automatically. In the preferred embodiment, spell checking and abbreviations are flagged, and the medical coder corrects the 'errors' with assistance by the system.

The medical coder can add annotations to sentences in the validation window to resolve ambiguous anaphora. For example, in the following mammography report: Description: (1) The breasts are heterogeneously dense. (2) This reduces the sensitivity of mammography. (3) No suspicious lesions are evident. Impression: (4) No mammographic evidence of malignancy. The medical coder in line two could add the annotation <<The heterogeneously dense breasts>> reduces the sensitivity of mammography. By adding this annotation the ambiguous, 'This', is replaced with the antecedent, which improves coding precision. If any sentence is changed by the medical coder it is marked as modified in the 'code view'. The original unmodified text is always retained.

The document is validated against a document type definition to ensure that the overall structure is codeable. This includes checking for duplicate headers, more than one sentence per line, incorrect abbreviations, etc., but may include other rules as determined for a specific document type. A graphic symbol, such as green dot, is generated if the document validates correctly, and a red dot if the document does not validate correctly, so additional changes in the document can be made prior to coding.

The next step in the process is matching the sentences to semantic propositions created by the earlier invention, corpus based knowledge construction. In that invention, each unique sentence in a document collection is mapped to one or more semantic proposition(s), which represent the semantic knowledge of a sentence. The present invention uses the proposition mapping table created by that invention. The 'code page' displays the proposition(s) that represent the semantic information for each sentence. This view also shows the line number of the underlying sentence (from the validation window) and allows the medical coder to either include or exclude these propositions prior to the next step of the coding process, mapping propositions to codes in the standard lexicon.

Sentences may be identified in this phase, which have never been seen by the system. Some of these sentences may not be important for coding and will be ignored by the medical coder. Others must be added to the table of unique sentences for the domain. After the sentences are added their semantics can be determined. A knowledge editor tool, fully described in corpus based knowledge construction, assists knowledge engineers in this task. Some sentences may be known by the system but have unknown semantics. This may be the result of a backlog of sentences waiting to be mapped to their logical propositions. The medical coder can send these sentences to the knowledge editor tool marked with a higher priority. The medical coder also has the option of preventing propositions from being matched to codes in the standard lexicon code. This option might be considered if the sentence was not considered important enough to code by a specific organization.

The last step is matching propositions to codes in the standard lexicon. For SNOMED CT, a display window would show all of the codes which map each proposition and the quality of the match as judged by a medical expert. Prior to this step, a code mapping table is created with a software utility that will be fully described. Using this utility the quality of every match from a proposition to a standard code is rated by a medical expert.

Explanation of Figures

With this in mind.

Window (105) shows segmented text that has not been validated. Every valid document must conform to a corresponding document type definition—DTD. A DTD defines the legal building blocks of a valid document. In a DTD, the structure of a particular type of document is described via element and attribute-list declarations. The use of DTDs is well known understood by those in the art of publishing and computer science. In the preferred embodiment, the DTD specifies that no more than a single header exists for each sentence. It also specifies no more than one sentence per line. Reports with duplicate headers are also flagged as invalid. However, the nature of DTDs allows them to be extensible and customizable to many document types. For this example, additional rules can be easily added based on the feedback from coding actual reports. Different DTDs also can be used for different medical reports. Validating documents against a DTD helps reduce automated coding errors. Prior to validation incorrectly spelled words and abbreviations are flagged (not shown). The medical coder can correct the spelling by 'right clicking' on the word, using a medical dictionary, well known to those in the art of word processing. Abbreviations can be expanded through the same method. Alternatively, abbreviations can be expanded using regular expressions. If changes are made to the document, a visual marker (red vertical line) is generated to the right of the line number. Other visual cues could be used depending on the designer's preference.

After corrections are made and the medical coder is satisfied the document appears valid, the button (107), 'Validate', is pressed. If the revised document is in conformance with the DTD and contains no spelling or abbreviation errors, a green dot appears next to the button to indicate the coding process has started. Otherwise, a red dot appears next to the button and the offending lines are marked with red ovals in the gutter of Window (105) to indicate additional corrections are needed, prior to coding.

The user can display a new report for segmentation and coding using slider 109, or can review past coded reports.

Figure 1:
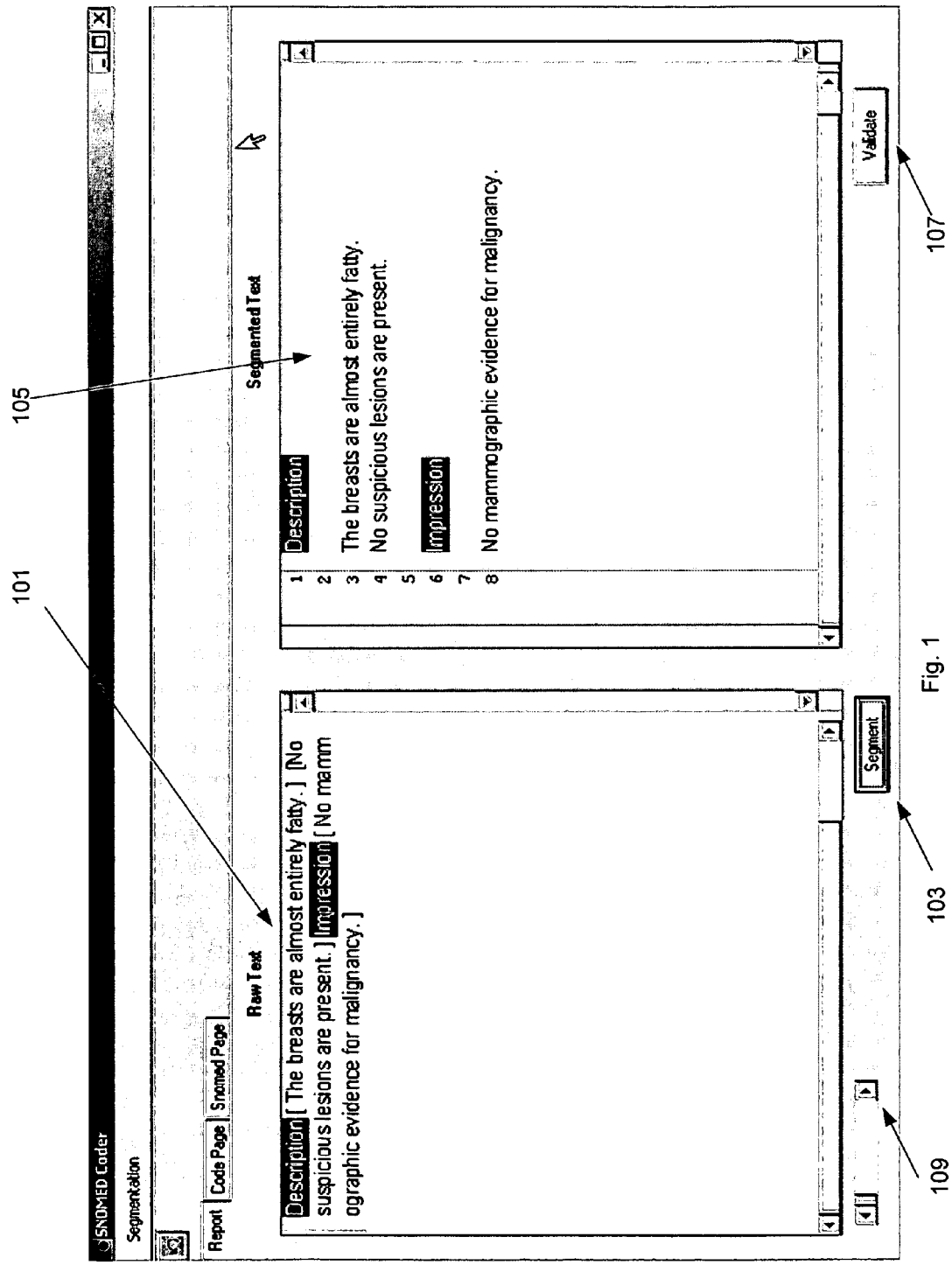
FIG. 1 depicts the visual interface of the coding system that implements the first step of the invention—segmentation. Prior to coding the system must identify the headers and sentence boundaries in the document. Window (101) depicts the display of a short radiology report where each of the headers has been highlighted in inverse video, and each sentence has been delimited with brackets. The report is the 'raw text', meaning there has been no annotation other than identifying headers and delimiting sentences. The segmentation process is configurable so that either automatic or manual segmentation can be performed. In the preferred embodiment, automatic segmentation performs sentence boundary detection using hidden markov models and training data to predict the beginning and end of sentences. This method is well known to those in the art of natural language processing, but a variety of other algorithms could be used as well. However, even the most sophisticated automated methods are only 99% accurate. The present invention allows the user to move the beginning or ending sentence bracket to re-delimit the sentence boundaries if automatic segmentation is in error. The system uses regular expressions to detect document headers. For the report in Window (101) this includes: 'History', 'Procedure', 'Source', 'Description', and 'Impression'. The use of regular expressions to detect relatively simple text patterns is well known in the field of computer science. Because even complex rules may miss some document headers, the medical coder can manually delimit headers should the automated approach fail. The button (103) labeled, 'Segment', is used to create display Window (105) after the medical coder is satisfied that segmentation is correct. Each header and sentence is placed on a separate line for easy identification on the 'code page'.
Figure 2:
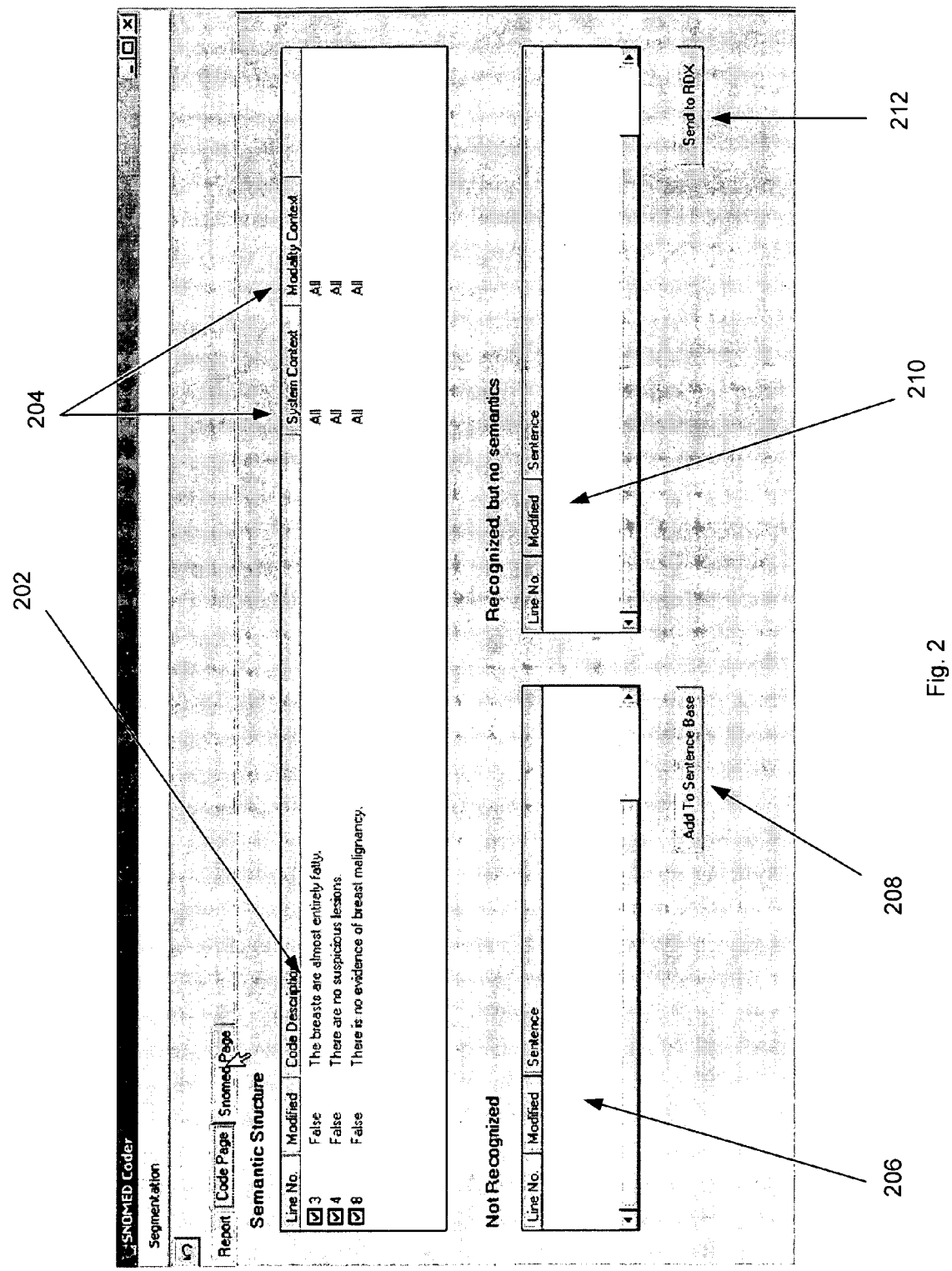

FIG. 2 shows the results of semantic analysis for a validated report in FIG. 1. The top window shows the semantic proposition(s), which map the semantic content of the sentences in the segmented report. In this case there is only one proposition per sentence, but for compound sentences there would usually be two or more propositions. Each proposition has a unique identifier, which represents the semantic knowledge of some part of the sentence. Window segment (202) shows the proposition's description. Notice for line number eight, the semantic proposition is 'There is no evidence of breast malignancy', although the sentence in the report is 'No mammographic evidence of malignancy.' Propositions are different from sentence expressions although they are related. Corpus based knowledge construction teaches how this mapping is constructed. The present invention uses the proposition mapping table from that invention to look up the sentence string in the proposition mapping table to retrieve the matching proposition(s). The sentence may be normalized to remove terminal periods or other characters prior to matching. In the preferred embodiment an exact match is required. However, alternate approaches using inexact vector based matching can be used if lower precision is acceptable.

Because free text can be semantically ambiguous, using information that applies only to some documents and not others can be helpful for disambiguation. In the case of radiology reports system context and modality context (204) are two such properties. Their use is described in corpus based knowledge construction, but briefly they refer to the region of the body examined (system context), and the type of imaging equipment used (modality context). For other domains different context markers would be used. For the illustrated embodiment, these properties help disambiguate sentences that could have multiple meanings in radiology. For example, the sentence 'There is no evidence of effusion' would mean 'There is no evidence of pleural effusion' in the chest system context, and 'There is no evidence of a knee effusion' in an x-ray of the lower extremity context. If the system and modality context is not provided as part of the document's metadata, the medical coder can simply select the correct context based on their knowledge of the report. The context markers are retrieved from the proposition mapping table.

Window 206 displays all the segmented sentences from the report which are not be found in the unique sentence table first created with corpus based knowledge construction. If a medical coder desires, this can be added to the unique sentence table for this domain by clicking on button (208). At this point the semantics of this sentence are still unknown. However, the semantics can be assigned through the knowledge editing tool of corpus based knowledge construction.

Window 210 displays all the segmented sentences that are found in the unique sentence table, but do not have any corresponding entries in the proposition mapping table. The medical coder can send these sentences with high priority to the knowledge editor by clicking on button 212. In the preferred embodiment this is done through a message queue, but this could be accomplished by other means by those knowledgeable in computer engineering. After determining the semantics of the sentence, the codes in the standard lexicon are assigned.

FIG. 3 shows the SNOMED CT codes corresponding to the propositions in the upper window of FIG. 2. Column 303 shows the proposition description, column 305 displays the quality of the match, column 307 the SNOMED CT concept identifier, and column 309 the part of the proposition (phrase) that the SNOMED CT concept represents. Label 311 depicts the fully qualified name for each SNOMED CT concept. Note for the first proposition, 'The breast are almost entirely fatty', the SNOMED CT concept contains a multi-word term 'Breast almost entirely fatty', that closely matches the proposition. This is a good example of where a SNOMED CT concept is 'pre-coordinated', containing not only a head noun but several modifiers. However, the second proposition, 'There are no suspicious lesions', needs three SNOMED CT codes, to represent the semantic knowledge, because there is no pre-coordinated concept. The present invention characterizes the document's semantics with both logical proposition (s) and codes from a standard lexicon. Thus, if the standard lexicon adopted a new pre-coordinated concept, 'No suspicious lesions', it would be relatively straightforward to update the standard codes for this document.

The codes are retrieved from the code mapping table, which maintains an association between a proposition and codes in the standard lexicon using a foreign key. A separate code mapping table must be created for each standard lexicon, such as ICD-9, LOINC, SNOMED CT, etc., that the document is to be matched against. A software utility assists in building these tables which will be fully described. One important aspect of building this table is rating the quality of matches between the propositions and codes in the standard lexicon. Unfortunately, most lexicons are not created from the vantage point of the document's semantics. Thus, there may be propositions (propositions are always created to reflect the semantics of sentences in documents) which have poor or no representation in the standard code set.

Because medical experts are able to consider the entire coding context, they are able to rate the quality of the code match. For example, SNOMED CT does not have any codes that adequately reflect the semantics of propositions like, 'There is blunting of the costophrenic angles', 'The thoracic spine is in anatomic alignment', and 'The left hemidiaphragm remains obscured'. The current invention keeps track of these mismatches, and provides a mechanism for a standard's body, such as SNOMED CT, to receive feedback to improve their code coverage.

Figure 4:
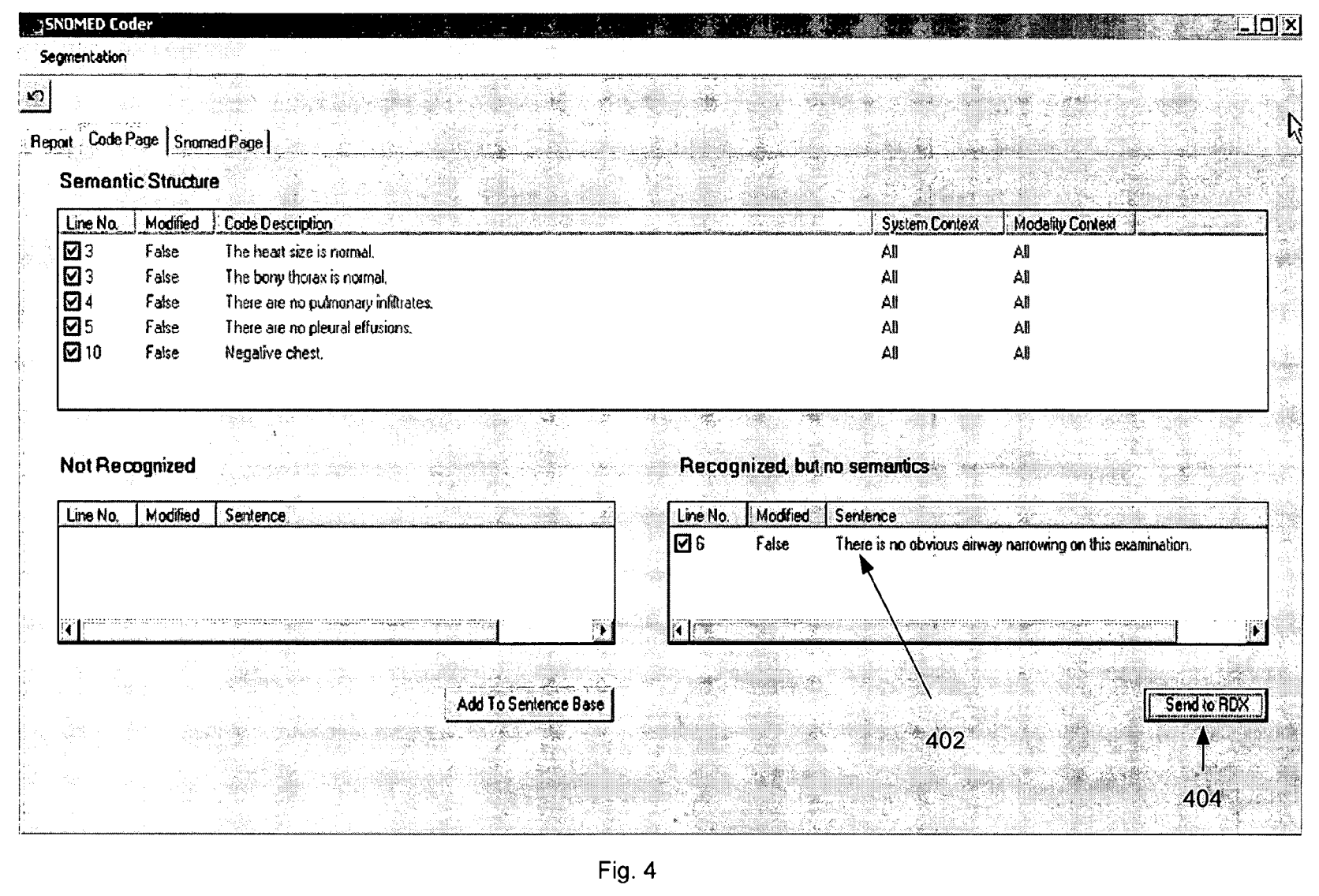

With reference to FIG. 4, notice that the sentence 402, "There is no obvious airway narrowing on this examination", is contained in the unique sentence table, but does not have any associated semantic proposition(s). The system detected this state through a simple lookup operation in the proposition mapping table. In this example, the medical coder checked this sentence and sent it to the knowledge editor by 'clicking' button 404.

Figure 5:
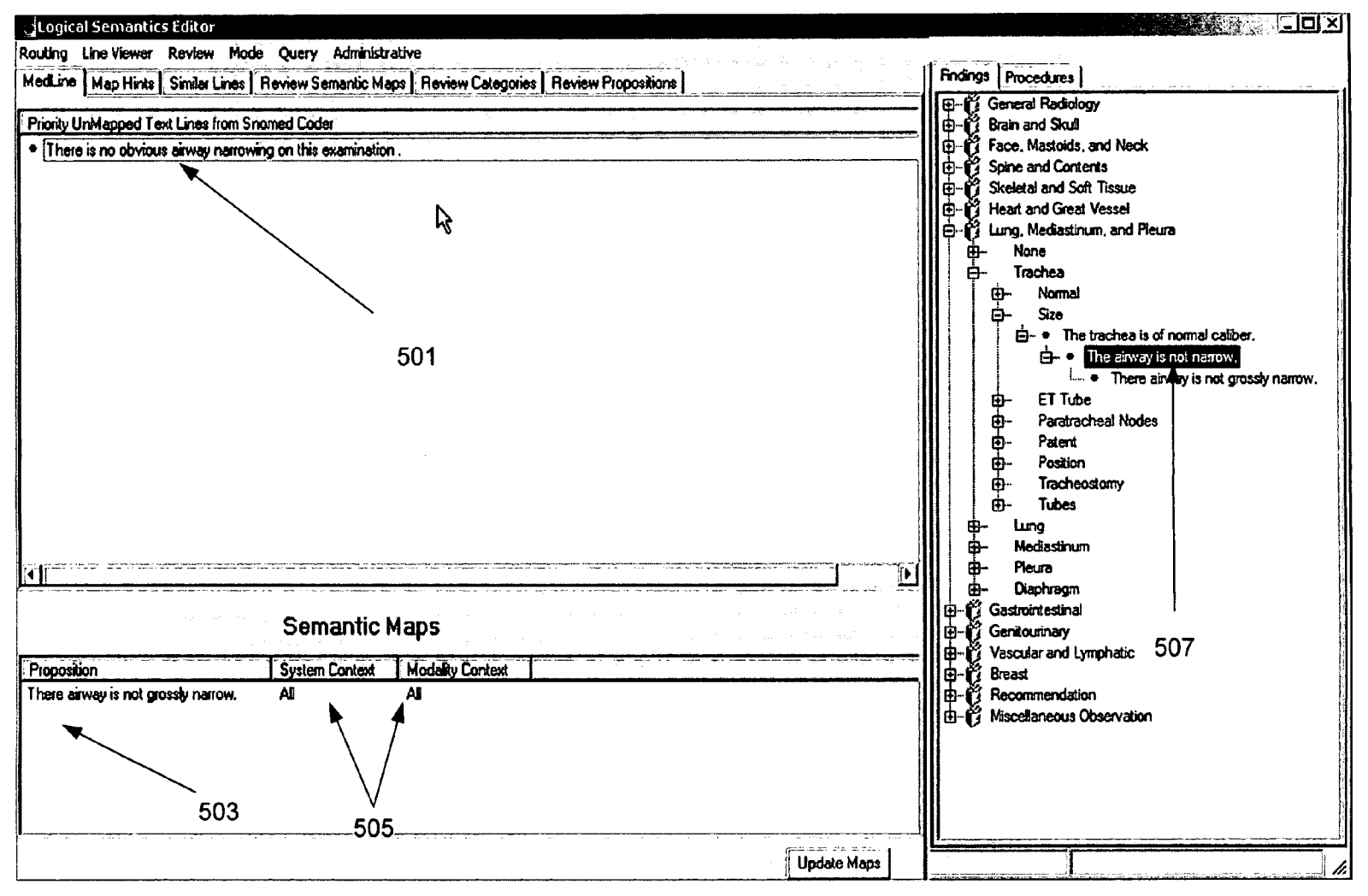

FIG. 5 shows the knowledge editor, whose operation in fully described in corpus based knowledge construction. For this example, there was no exact semantic match to the sentence, "There is no obvious airway narrowing on this examination." The closest proposition was, 'The airway is not narrow.' A new proposition was created directly below this proposition in the knowledge hierarchy, 'The airway is not grossly narrow.' This proposition was then mapped to the sentence so that its semantics could be defined.

Figure 6:
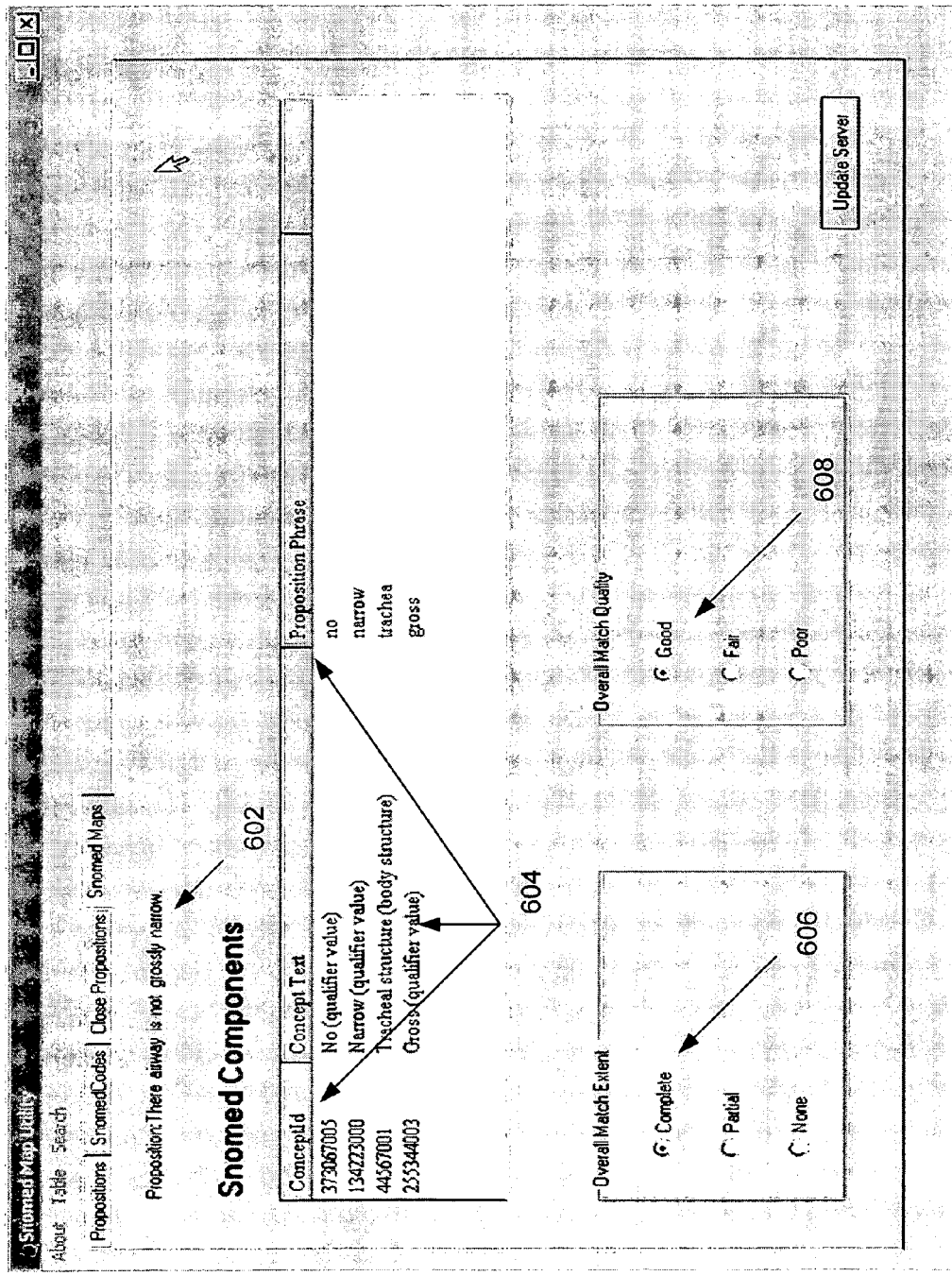

FIG. 6 shows one aspect of the code mapping utility. The proposition to be mapped, 'The airway is not grossly narrow' is shown in label 602. The SNOMED components (604) are identified in a list view, where the 'Concept ID' is the SNOMED CT identifier, the 'Concept Text' is the description of the SNOMED CT concept, and the 'Proposition Phrase' is that part of the overall proposition the SNOMED CT concept matches. In this example, four SNOMED CT concepts are needed to capture the semantic meaning of the proposition. Because taken together they span all the critical words in the proposition, the knowledge engineer, rates the match as 'Complete' (606). Since the fidelity of the semantics is very close, the knowledge engineer, rates the match quality as 'Good' (608). The selection of SNOMED CT codes is made by comparing the words in the proposition to code descriptions in the SNOMED CT table. In the exemplary embodiment, the strings are compared using the "free-text table" predicate (found in the full text search engine of the Microsoft™ Sql2000 RDBMS), and the list is sorted in descending rank order by minimum edit distance. If the knowledge engineer does not find a good match using this method, he/she can use the CLUE-5 Runtime Terminology Browser™ from the Clinical Information Consultancy to navigate the SNOMED CT hierarchy and find the best match. Additionally, full text search is also applied to propositions that have been previously mapped to SNOMED CT codes. Often closely related propositions share one or more SNOMED CT codes. The mapping utility displays these codes and allows the knowledge engineer to select them through a checkbox. While the mapping utility speeds the assignment of codes from the standard lexicon to proposition (s), the same results can be achieved by creating mapping entries directly by inputting SNOMED CT concept identifiers learned from various reference sources. The present invention does not require a specific method for creating the code mapping table. Those knowledgeable in the art of free text database search may implement other methods for creating this table.

FIG. 7 shows all the SNOMED CT concepts from the validated report corresponding to the propositions in FIG. 4. Line 701 shows the SNOMED CT code '44567001' (column 707), the part of the proposition phrase 'trachea' (column 709), and the match quality, 'good' (column 705). Label 703 depicts the fully qualified name for SNOMED CT concept, 'Tracheal structure (body structure)', taken from the SNOMED CT concept table. The College of American Pathology publishes and distributes SNOMED CT in tab delimited tables, which are easily imported into relational database tables. The medical coder has the option of including or excluding each SNOMED CT code from semantic analysis of the free text report. Depending on the coder's preference the codes can be stored in a relational database along with the report, or the codes can be embedded in the metadata of the report, or both.

Figure 8:
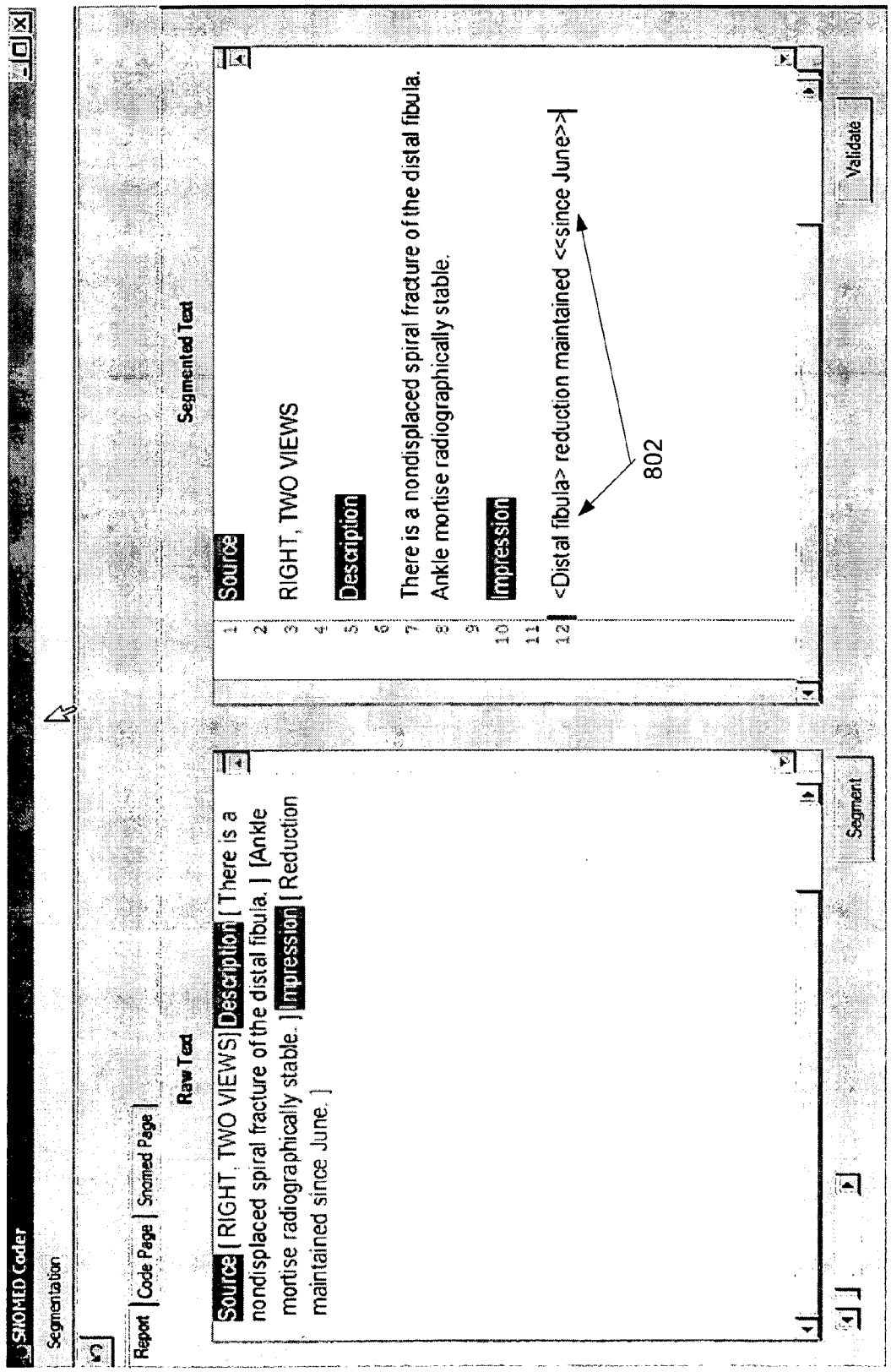

FIG. 8 shows another aspect of the invention which enables a medical coder to modify a segmented line from the report in order to disambiguate anaphora. The original line 802 read, 'Reduction maintained since June'. The modified line reads 'Distal fibula reduction maintained'. By adding the antecedent 'Distal fibula', the medical coder has made it clear what bone has been reduced. The medical coder has also decided to drop the phrase 'since June' because it does not add value for the purpose of coding (the original text of the report is always saved). The modified sentence will now be coded with much higher precision than the original sentence. Note the darkened vertical line next to line 12. This makes it clear the line has been modified.

Figure 9:
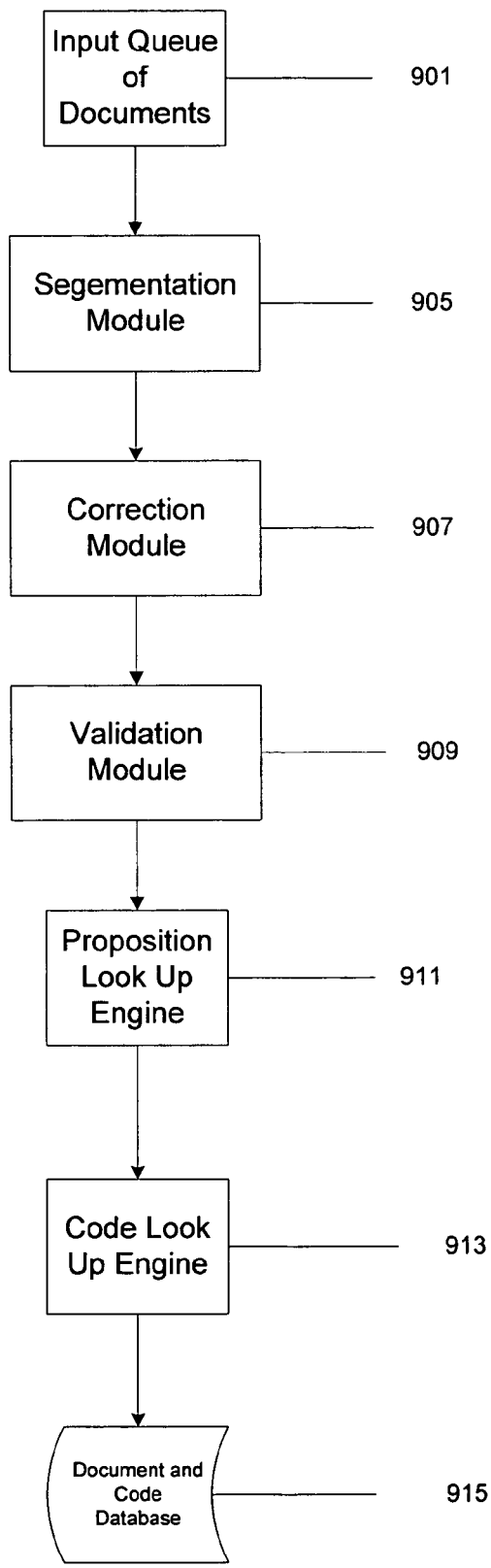

FIG. 9 depicts a very-high level block diagram of the components of the semantic coding system. The overall system consists of an input queue of documents (901) that will be coded through the present invention. This queue can accept documents from a number of sources including a desktop PC, computers connected to a local network, or a wide area network such as the internet. In the preferred embodiment, the queue is created using Microsoft Message Queuing™, but those knowledgeable in the art of computer science can use any number of middleware systems. The segmentation module (905) divides the documents into headers and sentences. The module performs sentence boundary detection using hidden markov models and training data to predict the beginning and end of sentences. The user can over ride the automatic segmentation. The correction module (907) flags incorrectly spelled words and abbreviations using a spelling dictionary and regular expressions. The user can correct the errors with computer assistance well known to those in the art of word processing. The validation module (909) checks the document against a document type definition (DTD) which varies by document type. The proposition look up engine (911) uses the sentence to proposition mapping table (1006) to locate the proposition(s) corresponding to the sentence. Tables (1006, 1014) will be described in more detail in FIG. 10. In the preferred embodiment, the sentence (string) is a foreign key for table 1006. The code look up engine (913) uses the proposition to code mapping table (1014) to locate the codes in the standard lexicon corresponding to the proposition. In the preferred embodiment, the proposition identifier is a foreign key for table 1014. After coding takes place the codes, annotated and corrected document, and original document are saved in a database (915). For the preferred embodiment, SQL Server 2000™ is used but any relational database could serve an equivalent purpose.

Figure 10:
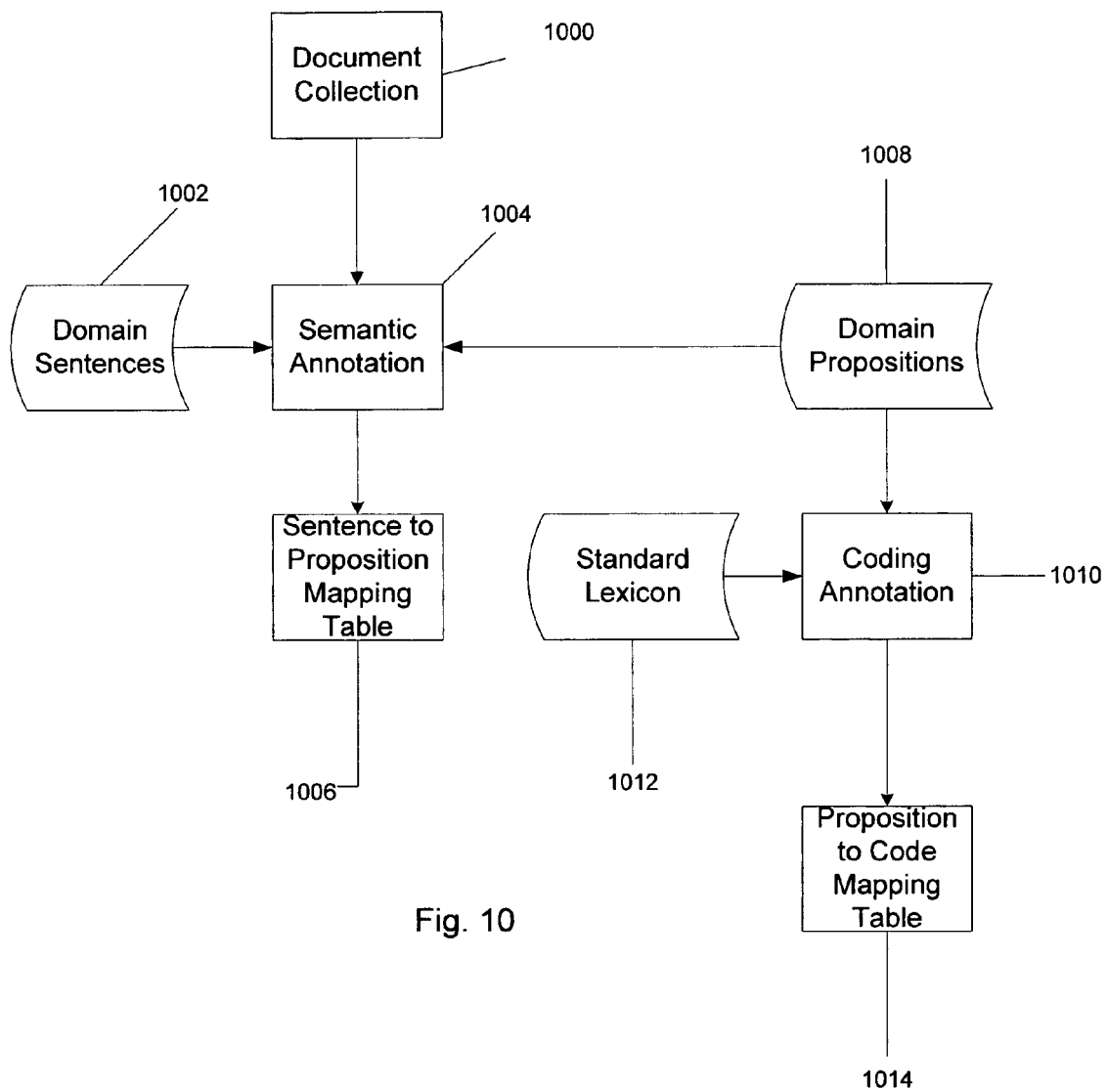

FIG. 10 shows the process for creating the two mapping tables (1006, 1014) used by the components (911, 913). Some of these steps are explained in detail in corpus based knowledge construction. A document collection, (1000) or corpus defines the knowledge domain and provides documents to be semantically characterized. The document collection is segmented into unique sentences (1002). Unique propositions (1008) are then created, which codify the meaning of these sentences, using the process and methods taught in corpus based knowledge construction. A knowledge engineer using semi-automated methods performs semantic annotation (1004) of the sentences (1002) selecting one or more propositions defined in (1008) to construct the proposition mapping table (1006). The mapping table is able to associate linguistic expressions (sentences) with their underlying semantic meaning. After the domain propositions are created (1008), they are matched with the code mapping utility of the present invention to the codes in the external or standard lexicon (1012), using the process of code annotation (1010) previously described. The result is a proposition to code mapping table (1014). One of these tables must be created for each standard lexicon the document coder desires to code against using the present invention.

Figure 11:
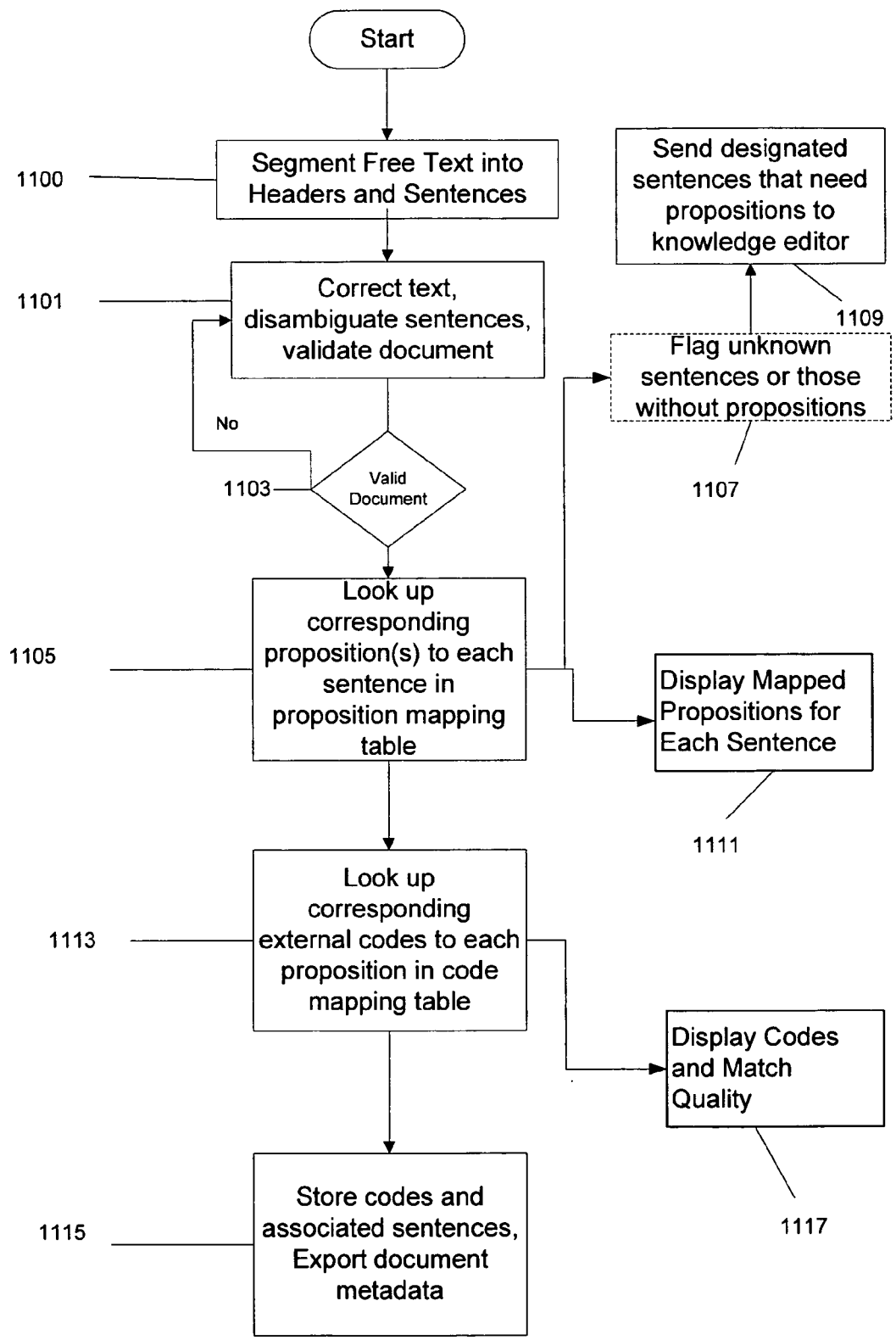

FIG. 11 shows a flowchart for performing high precision semantic coding. All the operations can be performed with a general purpose computer system. Prior to coding, a set of reports is queued up for the system and the medical coder. The first report is selected. In step (1100) the free text is segmented into headers and sentences. The segmented text is displayed on individual lines. The medical coder then corrects spelling errors, abbreviations, document formatting errors, and annotates lines that are ambiguous (1101). The system assists the medical coder by identifying errors. At the end of step 1101, the document is validated against the DTD (1103) and if it is in conformance, proceeds to step 1105. If not, further corrections are made. The system then looks up all the propositions associated with these sentences (1105) using the sentence to proposition mapping table (1006). If unknown sentences (sentences not in the unique sentence table) are discovered, they are flagged (1107). Sentences with unknown semantics (no matching propositions) are also flagged (1107). The medical coder has the option to send these sentences to the knowledge editor for semantic definition (1109). Sentences with known semantics (matching propositions) are displayed in step 1111.

Continuing with step (1113), the foreign key for each proposition is looked up in the standard code table and the matching codes (including the quality of the match) are displayed in step 1117. Finally, the codes, associated sentences and propositions, and the document itself are stored in a separate relational database table (115). The codes and related semantic information are also embedded in the report's metadata.

The method of the present invention can be realized in a centralized fashion in one computer system or in a distributed fashion where different elements are spread across interconnected computer systems over a network. A typical combination of hardware and software consist of a general purpose server computer system employing a relational database engine for storing and retrieving documents, sentences, propositions, lexicons, and mapping tables. A separate client computer using a microprocessor and software program could display the visual interface for the coding application and produce the screen displays shown in FIGS. 1, 2, 3, 4, 5, 6, 7, and 8. The client machine communicates to the database engine over a computer network, which may consist of either an intranet or wide area network such as the internet. In the preferred embodiment the programming platform includes C#.NET™ and ADO.NET™ for building the client query application, and SQL-Server™ for building the relational database engine and server application. However, nothing about the described invention requires this combination of computing resources or languages. Any relational database engine could be used to construct the semantic coding application. The client or server software could be constructed to include program modules consisting of objects, components, data structures, stored procedures, etc. that implement particular tasks of the overall program. Moreover, those skilled in the art will appreciate that the invention may be practiced with other computer system configurations, including handheld devices, multiprocessor systems, microprocessor-based or programmable consumer electronics, network PCs, minicomputers, mainframe computers, and the like. For a distributed computing environment, program modules may be located in both local and remote memory storage devices. Those versed in the art of computer programming will appreciate the wide range of platforms and software elements which could be used to create particular embodiments of the invention.

DESCRIPTION AND OPERATION OF ALTERNATIVE EMBODIMENTS

The system could work in a fully automated mode. In this mode, segmentation would be fully automatic. However, because corrections would be automatic and annotations would not be possible, the resulting propositions and codes from the standard lexicon would not be as precise. Additionally, the system would need to be configured to automatically decide how to dispose of unknown sentences or those with unknown semantics. For example, all unknown sentences could be added to the unique sentence table. However, this may be undesirable for protecting patient privacy.

Different types of string comparisons could be done other than an exact match in step 1105. Although an exact match will provide for the highest precision, recall can be improved by relaxing this constraint. One approach could use the Microsoft™ "contains" or "freetexttable" SQL predicates. Other similarity metrics such as the minimum edit distance could be used alone or in combination by those knowledgeable in the art of string pattern matching. The propositions and codes could be displayed, and if the user felt they were similar enough, retained as part of the coding solution.

Advantages

From the description above, a number of advantages for my method of high precision coding of free text documents against a standard lexicon become evident:

The coding system has very high precision because the meaning/semantics of the sentences in the document are established by medical experts using the entire context of the sentence and the document, rather than relying on the crude matching algorithms used by other autocoders.

The entire document can be coded efficiently in contrast to other systems which only code against a particular subset of standard codes.

The medical coder is able to intervene in the process to better segment, correct, and annotate documents so coding is more accurate in contrast to fully automated systems.

The system is able to report the quality of the coding match in an intuitive way most useful to a medical coder.

The system is able to constantly learn new sentences and semantics.

The system can work with a number of standard lexicons and should changes occur in the standard lexicon, documents that have been previously coded with the old terminology can be easily updated without rework.

Document sentences that contain privileged information can easily be excluded from analysis.

The system works in near real-time since indices and mapping tables are pre-computed.

The resulting codes can be easily embedded in the document's metadata to facilitate precise information exchange.

Although the description above contains many specifics, these should not be construed as limiting the scope of the invention but merely providing illustrations of some of the presently preferred embodiments. Thus the scope of the invention should be determined by the appended claims and their legal equivalents, rather than by the examples given.

What is claimed is:

1. A computer implemented method for assigning codes from a standard lexicon to a free text document describing physical or tangible objects, the method comprising the steps of:
    (a) automatically segmenting said free text document into a plurality of sentences;
    (b) using a computer processor to retrieve a plurality of propositions by matching said sentences in a semantic mapping table created by domain experts through semantically annotating sentences from a corpus of related documents in a knowledge domain to propositions,
    (c) using a computer processor to retrieve a plurality of codes in a standard lexicon by matching said propositions to said codes created by a third party, in a code mapping table created by domain experts by annotating said propositions to said codes;
    wherein one or more of said matching codes from said standard lexicon represents at least a portion of the semantic content of said free text document.

2. The method according to claim 1 further comprising a step of correcting the segmented document prior to step c.

3. The method according to claim 1 further comprising a step of resolution prior to step c.

4. The method according to claim 1 further comprising a step of validation prior to step c.

5. The method according to claim 1, wherein sentences without known propositions determined through step b are displayed and are optionally sent to a knowledge engineer for semantic annotation prior to step c.

6. The method according to claim 1, wherein the matched propositions in step b are displayed, and optionally excluded from step c by the user.

7. The method according to claim 1, wherein the matched codes from the standard lexicon are displayed.

8. The method according to claim 1, wherein sentences without matching codes from the standard lexicon are identified.

9. The method according to claim 1, wherein the semantic match quality of the matched codes from the standard lexicon as determined by a domain expert are displayed.

10. The method according to claim 1, wherein sentences with a match quality other than 'good' as determined by a domain expert are displayed.

11. The method according to claim 1, wherein the matched codes from the standard lexicon are stored in a database.

12. The method according to claim 1, wherein the matched propositions are stored in a database.

13. The method according to claim 1, wherein the matched codes from the standard lexicon are added to the document's metadata.

14. The method according to claim 1, wherein the matched codes from the standard lexicon are optionally excluded by the user.

15. The method of claim 1, wherein the document is a physician note or report.

16. The method of claim 1, wherein the standard lexicon is selected from the group consisting of: (a) SNOMED CT (b) ICD-9-CM, (c) ICD-10, (d) HCPCS, (e) NDC, (f) CPT, (g) UMLS, (h) LOINC, (i) CDPN, (j) DRG.

17. The method of claim 1, wherein the standard lexicon is either pre-coordinated or compositional.

18. The method of claim 1, wherein the segmentation is completely automatic and optionally modified by the user.

19. A system for assigning codes from a standard lexicon to a free text document, codes, comprising:
   (a) an input queue of documents; and
   (b) a segmentation module for processing free text into headers and sentences; and
   (c) a proposition look up engine that associates said segmented sentences with a plurality of propositions using a semantic mapping table created by domain experts through a process of semantically annotating sentences from a corpus of related documents in a knowledge domain to propositions; and
   (d) a code look up engine that associates said propositions with a plurality of codes from a standard lexicon using a code mapping table created by domain experts through a process of annotating said propositions to said codes.

20. The system of claim 19, further comprising a module for correcting free text.

21. The system of claim 19, where errors are displayed with a property that provides a visual indication that distinguishes it from normal text such as a different color, font, size, highlighting, underlining, label, or any combination.

22. The system of claim 19, further comprising a module for validating free text against a document type definition.

23. The system of claim 19, where codes from the standard lexicon are added to the document's metadata.

24. The system of claim 19, where matched propositions are stored in a database.

25. Computer readable media having computer readable instructions for assigning codes from a standard lexicon to a free text document, the instructions comprising:
   (a) instructions for segmenting said free text document into a plurality of sentences;
   (b) instructions for retrieving a plurality of propositions by matching said sentences in a semantic mapping table created by domain experts through-semantically annotating sentences from a corpus of related documents in a knowledge domain to propositions,
   (c) instructions for retrieving a plurality of codes in a standard lexicon by matching said propositions, to said codes created by a third party in a code mapping table created by domain experts by annotating said propositions to said codes;
   wherein one or more of said matching codes from said standard lexicon represents at least a portion of the semantic content of said free text document.

* * * * *